United States Patent
Shigeta et al.

(10) Patent No.: US 10,839,976 B2
(45) Date of Patent: Nov. 17, 2020

(54) SILICONE RUBBER COMPOSITION AND VULCANIZED PRODUCT

(71) Applicant: ZEON CORPORATION, Tokyo (JP)

(72) Inventors: Masahiro Shigeta, Tokyo (JP); Tsutomu Nagamune, Tokyo (JP); Arinobu Katada, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 15/551,910

(22) PCT Filed: Feb. 26, 2016

(86) PCT No.: PCT/JP2016/001061
§ 371 (c)(1),
(2) Date: Aug. 18, 2017

(87) PCT Pub. No.: WO2016/136275
PCT Pub. Date: Sep. 1, 2016

(65) Prior Publication Data
US 2018/0044498 A1  Feb. 15, 2018

(30) Foreign Application Priority Data
Feb. 27, 2015  (JP) .................. 2015-038730

(51) Int. Cl.
*H01B 1/18*  (2006.01)
*C08K 3/04*  (2006.01)
(Continued)

(52) U.S. Cl.
CPC .............. *H01B 1/18* (2013.01); *C08K 3/041* (2017.05); *C08L 83/04* (2013.01); *C08K 7/06* (2013.01);
(Continued)

(58) Field of Classification Search
CPC ... H01B 1/04; H01B 1/18; H01B 1/24; C08K 3/04; C08K 3/041; C08K 2201/001;
(Continued)

(56) References Cited

U.S. PATENT DOCUMENTS 7,150,840 B2 * 12/2006 Yamamoto ............. B82Y 30/00
252/500
7,585,484 B2 * 9/2009 Liu ........................ B01J 3/006
423/447.1
(Continued)

FOREIGN PATENT DOCUMENTS

CN  103165742 A  6/2013
CN  104302707 A  1/2015
(Continued)

OTHER PUBLICATIONS

Mar. 29, 2016, International Search Report issued in the International Patent Application No. PCT/JP2016/001061.
(Continued)

*Primary Examiner* — Matthew R Diaz
(74) *Attorney, Agent, or Firm* — Kenja IP Law PC (57) ABSTRACT

Disclosed is a silicone rubber composition and a vulcanized product thereof, which show high levels of flexibility and electrical conductivity at the same time. The disclosed silicone rubber composition comprises a silicone rubber and fibrous carbon nanostructures including carbon nanotubes, wherein the fibrous carbon nanostructures exhibit a convex upward shape in a t-plot obtained from an adsorption isotherm. The disclosed vulcanized product is obtainable by vulcanization of the silicone rubber composition.

9 Claims, 1 Drawing Sheet

(51) Int. Cl.
*C08L 83/04* (2006.01)
*C08K 7/06* (2006.01)
*C08K 7/24* (2006.01)

(52) U.S. Cl.
CPC .......... *C08K 7/24* (2013.01); *C08K 2201/001* (2013.01); *C08K 2201/003* (2013.01); *C08K 2201/006* (2013.01); *C08K 2201/011* (2013.01); *Y10S 977/75* (2013.01); *Y10S 977/753* (2013.01); *Y10S 977/843* (2013.01); *Y10S 977/932* (2013.01)

(58) Field of Classification Search
CPC ........ C08K 2201/003; C08K 2201/006; C08K 2201/011; C08K 7/06; C08K 7/24; C08L 83/04; C01B 32/158; C01B 32/159; C01B 32/16; C01B 32/162; C01B 32/164; C01B 32/166; C01B 32/168; C01B 32/17; C01B 32/172; C01B 32/174; C01B 32/176; C01B 32/178; C01B 2202/20; C01B 2202/24; C01B 2202/26; C01B 2202/32; B82Y 30/00; B82Y 40/00; Y10S 977/742; Y10S 977/743; Y10S 977/753
USPC .......................................... 977/742, 743, 753
See application file for complete search history.

(56) References Cited

U.S. PATENT DOCUMENTS

| | | | |
|---|---|---|---|
| 7,854,991 B2 | 12/2010 | Hata et al. | |
| 2003/0213939 A1* | 11/2003 | Narayan | B82Y 10/00 252/500 |
| 2004/0262581 A1* | 12/2004 | Rodrigues | B82Y 10/00 252/500 |
| 2008/0318049 A1* | 12/2008 | Hata | B82Y 30/00 428/408 |
| 2012/0148476 A1* | 6/2012 | Hata | B01J 23/74 423/447.3 |
| 2013/0157402 A1 | 6/2013 | Jin et al. | |
| 2014/0353556 A1 | 12/2014 | Shigeta et al. | |
| 2015/0123043 A1 | 5/2015 | Nagamune et al. | |
| 2016/0251225 A1* | 9/2016 | Takai | C01B 32/178 428/402 |
| 2018/0194122 A1 | 7/2018 | Kumamoto et al. | |

FOREIGN PATENT DOCUMENTS

| | | | | |
|---|---|---|---|---|
| EP | 2383225 A1 | * | 11/2011 | ............ B01J 23/745 |
| EP | 3064472 A1 | | 9/2016 | |
| EP | 3258489 A1 | | 12/2017 | |
| EP | 3315576 A1 | | 5/2018 | |
| JP | 2004338327 A | | 12/2004 | |
| JP | 2005521782 A | | 7/2005 | |
| JP | 4621896 B2 | | 1/2011 | |
| JP | 2013128116 A | | 6/2013 | |
| WO | 2003085681 A1 | | 10/2003 | |
| WO | 2006011655 A1 | | 2/2006 | |
| WO | WO-2006011655 A1 | * | 2/2006 | ............ B82Y 30/00 |
| WO | 2013080912 A1 | | 6/2013 | |
| WO | 2013172334 A1 | | 11/2013 | |
| WO | WO-2015064772 A1 | * | 5/2015 | ......... C01B 31/0286 |
| WO | 2016129257 A1 | | 8/2016 | |

OTHER PUBLICATIONS

Aug. 29, 2017, International Preliminary Report on Patentability issued in the International Patent Application No. PCT/JP2016/001061.
Aug. 28, 2018, the Extended European Search Report issued by the European Patent Office in the corresponding European Patent Application No. 16755025.0.
Database WPI Week 201705 Thomson Scientific, London, GB; AN2017-00033V, XP002783942, 2017.

* cited by examiner

SILICONE RUBBER COMPOSITION AND VULCANIZED PRODUCT

TECHNICAL FIELD

The present disclosure relates to silicone rubber compositions and vulcanized products.

BACKGROUND

Recently, rubber compositions containing a rubber such as silicone rubber blended with carbon nanotubes, and vulcanized products of the compositions have attracted attention as materials that exhibit superior electrical conductivity and mechanical properties (see, e.g., PTL 1 and PTL 2).

Silicone rubber compositions containing a silicone rubber blended with carbon nanotubes and vulcanized products of the compositions have been required to show high electrical conductivity while remaining flexible like rubber.

CITATION LIST

Patent Literature

PTL 1: WO2013/172334A
PTL 2: JP2004338327A

SUMMARY

Technical Problem

However, when a silicone rubber is blended with large amounts of fibrous carbon nanostructures such as carbon nanotubes for increased electrical conductivity, the silicone rubber composition and vulcanized product show increased hardness and thus low flexibility, resulting in poor adhesion and shape conformability during use.

Thus, there has been a need in the art to develop a silicone rubber composition and a vulcanized product thereof, which show high levels of flexibility and electrical conductivity at the same time.

Solution to Problem

The inventors have made extensive studies to achieve the foregoing object and established that the use of fibrous carbon nanostructures having a specific property would sufficiently increase the electrical conductivity of a silicone rubber composition and a vulcanized product thereof while limiting rises in their hardness. The inventors completed the present disclosure based on this finding.

Specifically, the present disclosure is aimed at advantageously solving the foregoing problem pertinent in the art, and the disclosed silicone rubber compositions comprise a silicone rubber and fibrous carbon nanostructures including carbon nanotubes, wherein the fibrous carbon nanostructures exhibit a convex upward shape in a t-plot obtained from an adsorption isotherm. When such fibrous carbon nanostructures that exhibit a convex upward shape in a t-plot obtained from an adsorption isotherm are blended, it is possible to sufficiently increase the electrical conductivity of the silicone rubber compositions while limiting rises in hardness.

For the disclosed silicone rubber compositions, the t-plot preferably has a bending point in a range of $0.2 \leq t\ (nm) \leq 1.5$. When fibrous carbon nanostructures are used that show a bending point in a range of $0.2 \leq t\ (nm) \leq 1.5$ in the t-plot, higher levels of flexibility and electrical conductivity can be attained at the same time.

For the disclosed silicone rubber compositions, total specific surface area S1 and internal specific surface area S2 which are obtained from the t-plot preferably satisfy the condition $0.05 \leq S2/S1 \leq 0.30$. When fibrous carbon nanostructures whose total specific surface area S1 and internal specific surface area S2 satisfy the condition $0.05 \leq S2/S1 \leq 0.30$ are used, higher levels of flexibility and electrical conductivity can be attained at the same time.

Further, for the disclosed silicone rubber compositions, the fibrous carbon nanostructures preferably have an average diameter of 2 nm to 10 nm. When fibrous carbon nanostructures having an average diameter of 2 nm to 10 nm are used, higher levels of flexibility and electrical conductivity can be attained at the same time.

The disclosed silicone rubber compositions preferably further comprise graphite. When the silicone rubber compositions further comprise graphite, it is possible to further increase electrical conductivity.

The present disclosure is aimed at advantageously solving the foregoing problem pertinent in the art, and the disclosed vulcanized product is obtainable by vulcanization of any one of the silicone rubber compositions described above. The vulcanized product obtainable by vulcanization of the silicone rubber composition is superior both in flexibility and electrical conductivity.

The disclosed vulcanized product preferably has a hardness of 80 or less. When the hardness is 80 or less, sufficient adhesion and shape conformability can be ensured during use.

The disclosed vulcanized product preferably has a volume resistivity of $10^5$ Ω·cm or less. When the volume resistivity is $10^5$ Ω·cm or less, the vulcanized product may be suitably used as an electrically conductive material.

Advantageous Effect

According to the present disclosure, it is possible to provide a silicone rubber composition and a vulcanized product thereof, which show high levels of flexibility and electrical conductivity at the same time.

BRIEF DESCRIPTION OF THE DRAWINGS

In the accompanying drawings.

DETAILED DESCRIPTION

Embodiments of the present disclosure will be described in detail below.

The disclosed silicone rubber composition comprises a silicone rubber and fibrous carbon nanostructures including carbon nanotubes, and optionally further comprises electrically conductive materials other than the fibrous carbon nanostructures (e.g., graphite) and/or additional additives. The fibrous carbon nanostructures of the disclosed silicone rubber composition exhibit a convex upward shape in a t-plot obtained from an adsorption isotherm. Further, the disclosed vulcanized product is obtainable by vulcanization of the disclosed silicone rubber composition. The disclosed silicone rubber composition and vulcanized product are superior both in electrical conductivity and flexibility and may be suitably used in any application, e.g., as materials for sealants, gaskets, electrodes, and connectors.

(Silicone Rubber)

Any silicone rubber can be used. Silicone rubbers known in the art can be used, e.g., polymers containing an alkylsiloxane unit such as dimethylsiloxane as the main component. The silicone rubber may have, in addition to the alkylsiloxane unit, small amounts of other structural units and/or functional groups. Further, where desired, the silicone rubber may be blended with additives known in the art, such as reinforcing fillers and/or lubricants. Examples of usable reinforcing fillers include reinforcing silica, quartz powder, iron oxide, alumina, and vinyl group-containing silicone resins.

Specifically, as the silicone rubber, millable silicone rubber or liquid silicone rubber can be used, for example.

(Fibrous Carbon Nanostructures)

Any fibrous carbon nanostructures including carbon nanotubes can be used as long as a t-plot obtained from an adsorption isotherm exhibits a convex upward shape. The fibrous carbon nanostructures may be composed solely of carbon nanotubes (hereinafter occasionally referred to as "CNTs") or may be a mixture of CNTs and electrically conductive fibrous carbon nanostructures other than CNTs.

When the silicone rubber is blended with fibrous carbon nanostructures that exhibit a convex upward shape in a t-plot obtained from an adsorption isotherm, it is possible to sufficiently increase the electrical conductivity of the silicone rubber composition while limiting rises in hardness.

It is more preferred that the fibrous carbon nanostructures including CNTs have not undergone CNT opening formation treatment as well as exhibit a convex upward shape in a t-plot Adsorption generally refers to a phenomenon in which gas molecules are taken away from the gas phase to a solid surface, and is classified as physical or chemical adsorption depending on the cause of adsorption. The nitrogen gas adsorption method used to acquire a t-plot utilizes physical adsorption. In general, when adsorption temperature is constant, the number of nitrogen gas molecules adsorbed to fibrous carbon nanostructures increases with increasing pressure. A plot of the adsorbed amount of nitrogen versus relative pressure (ratio of pressure P at adsorption equilibrium to saturated vapor pressure P0) refers to an "isotherm." An isotherm obtained when the adsorbed amount of nitrogen gas is measured while increasing pressure refers to an "adsorption isotherm" and an isotherm obtained when the adsorbed amount of nitrogen gas is measured while decreasing pressure refers to a "desorption isotherm."

A t-plot is obtained by converting relative pressure to average adsorbed nitrogen gas layer thickness t (nm) in an adsorption isotherm measured by the nitrogen gas adsorption method. Specifically, an average adsorbed nitrogen gas layer thickness t corresponding to a given relative pressure is calculated from a known standard isotherm of average adsorbed nitrogen gas layer thickness t plotted against relative pressure P/P0 and the relative pressure is converted to the corresponding average adsorbed nitrogen gas layer thickness t to obtain a t-plot for the fibrous carbon nanostructures (t-plot method of de Boer et al.).

Figure 1:
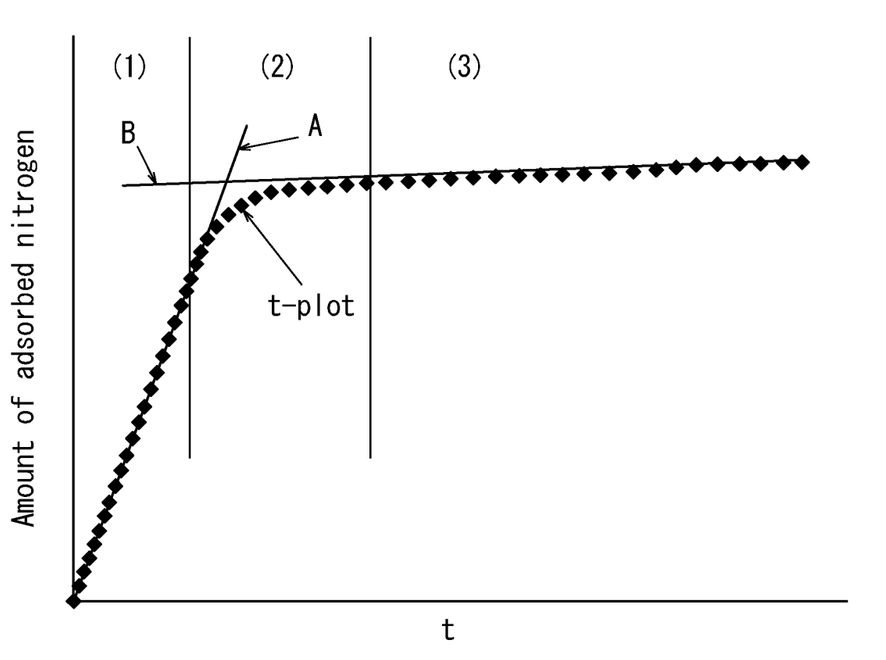
FIG. 1 is a graph of an example of a t-plot for a sample having pores at the surface.

FIG. 1 illustrates a typical t-plot for a sample having pores at the surface. The growth of an adsorbed layer of nitrogen gas for a sample having pores at the surface is divided into the following processes (1) to (3). The gradient of the t-plot changes according to processes (1) to (3) as illustrated in FIG. 1:

(1) a process in which a single molecular adsorption layer is formed over the entire surface by nitrogen molecules;
(2) a process in which a multi-molecular adsorption layer is formed in accompaniment to capillary condensation filling of pores; and
(3) a process in which a multi-molecular adsorption layer is formed on a surface that appears to be non-porous due to the pores being filled by nitrogen.

As illustrated in FIG. 1, the t-plot for fibrous carbon nanostructures including CNTs used in the present disclosure shows a straight line crossing the origin in a region in which the average adsorbed nitrogen gas layer thickness t is small, whereas the plot deviates downward from the straight line as t increases, showing a convex upward shape. Fibrous carbon nanostructures that exhibit such a t-plot curve have a large internal specific surface area relative to total specific surface area of the fibrous carbon nanostructures, indicating the presence of a large number of openings formed in the carbon nanostructures that constitute the fibrous carbon nanostructures. This is considered to result in fibrous carbon nanostructures exhibiting superior characteristics (especially electrical conductivity).

The t-plot for the fibrous carbon nanostructures including CNTs preferably has a bending point in a range of $0.2 \leq t$ (nm)$\leq 1.5$, more preferably in a range of $0.45 \leq t$ (nm)$\leq 1.5$, even more preferably in a range of $0.55 \leq t$ (nm)$\leq 1.0$. When the position of the bending point of the t-plot is within the range, characteristics (especially electrical conductivity) of the fibrous carbon nanostructures further improve allowing sufficient electrical conductivity to be imparted to the silicone rubber composition even when the blending amount of the fibrous carbon nanostructures is small. Hence, it is possible to sufficiently increase electrical conductivity while limiting reductions in flexibility.

The "position of the bending point" is an intersection point of an approximate straight line A for process (1) and an approximate straight line B for process (3).

The fibrous carbon nanostructures including CNTs preferably have a ratio of internal specific surface area S2 to total specific surface area S1 (S2/S1) of 0.05 to 0.30, obtained from the t-plot. When S2/S1 is 0.05 to 0.30, it is possible to further improve characteristics (especially electrical conductivity) of the fibrous carbon nanostructures while sufficiently limiting the formation of bundles, so that electrical conductivity of the silicone rubber composition can be sufficiently improved while limiting reductions in flexibility.

The fibrous carbon nanostructures including CNTs can have any total specific surface area S1 and any internal specific surface area S2. However, S1 is preferably 600 m²/g to 1,400 m²/g, more preferably 800 m²/g to 1,200 m²/g. On the other hand, S2 is preferably 30 m²/g to 540 m²/g.

Total specific surface area S1 and internal specific surface area S2 of the fibrous carbon nanostructures including CNTs can be found from the t-plot. Specifically, referring to the t-plot illustrated in FIG. 1, first, total specific surface area S1 can be found from the gradient of an approximate straight line corresponding to process (1) and external specific surface area S3 can be found from the gradient of an approximate straight line corresponding to process (3). Internal specific surface area S2 can then be calculated by subtracting external specific surface area S3 from total specific surface area S1.

Measurement of adsorption isotherm, preparation of a t-plot, and calculation of total specific surface area S1 and internal specific surface area S2 based on t-plot analysis for fibrous carbon nanostructures including CNTs can be made using for example BELSORP®-mini (BELSORP is a registered trademark in Japan, other countries, or both), a commercially available measurement instrument available from Bel Japan Inc.

Any type of CNTs may be used in the fibrous carbon nanostructures, such as, for example, single-walled carbon nanotubes and/or multi-walled carbon nanotubes, with single- to up to 5-walled carbon nanotubes being preferred, and single-walled carbon nanotubes being more preferred. The use of single-walled carbon nanotubes allows for further increases in electrical conductivity compared to the case where multi-walled carbon nanotubes are used.

The fibrous carbon nanostructures including CNTs are preferably those having a ratio of a standard deviation ($\sigma$) of diameters multiplied by 3 ($3\sigma$) to average diameter (Av) ($3\sigma/Av$) of greater than 0.20 to less than 0.60, more preferably those having $3\sigma/Av$ of greater than 0.25, even more preferably those having $3\sigma/Av$ of greater than 0.40. The use of fibrous carbon nanostructures including carbon nanotubes having $3\sigma/Av$ of greater than 0.20 to less than 0.60 allows for sufficient increases in electrical conductivity even when only small amounts of the fibrous carbon nanostructures have been blended, limiting rises in hardness (i.e., reductions in flexibility) of the silicone rubber composition due to blending of the fibrous carbon nanostructures including CNTs, so that a silicone rubber composition can be obtained that has sufficiently high levels of electrical conductivity and flexibility at the same time.

"Average diameter (Av) of fibrous carbon nanostructures" and "standard deviation ($\sigma$) (where $\sigma$ is sample standard deviation) of diameters of fibrous carbon nanostructures" can each be obtained by measuring the diameters (outer diameters) of 100 fibrous carbon nanostructures randomly-selected by transmission electron microscopy. The average diameter (Av) and standard deviation ($\sigma$) of the fibrous carbon nanostructures including CNTs may be adjusted either by changing the production method and/or the production conditions of the fibrous carbon nanostructures including CNTs or by combining different types of fibrous carbon nanostructures including CNTs, prepared by different production methods.

The fibrous carbon nanostructures including CNTs that are generally used typically take a normal distribution when a plot is made of diameter measured as described on the horizontal axis and the frequency on the vertical axis, and Gaussian approximation is made.

Furthermore, the fibrous carbon nanostructures including CNTs preferably exhibit a radial breathing mode (RBM) peak when evaluated by Raman spectroscopy. Note that no RBM appears in the Raman spectrum of fibrous carbon nanostructures composed solely of multi-walled carbon nanotubes having three or more walls.

In a Raman spectrum of the fibrous carbon nanostructures including CNTs, the ratio of G band peak intensity to D band peak intensity (G/D ratio) is preferably 1 to 20. A G/D ratio of 1 to 20 allows for sufficient increases in electrical conductivity even when small amounts of the fibrous carbon nanostructures have been blended, limiting rises in hardness (i.e., reductions in flexibility) of the silicone rubber composition due to blending of the fibrous carbon nanostructures including CNTs, so that a silicone rubber composition can be obtained that has sufficiently high levels of electrical conductivity and flexibility at the same time.

The fibrous carbon nanostructures including CNTs preferably have an average diameter (Av) of 2 nm or more, more preferably 2.5 nm or more, and preferably 10 nm or less, more preferably 6 nm or less. An average diameter (Av) of 2 nm or more can limit aggregation of the fibrous carbon nanostructures to increase the dispersibility of the fibrous carbon nanostructures. An average diameter (Av) of 10 nm or less can sufficiently increase the electrical conductivity and flexibility of the silicone rubber composition.

The fibrous carbon nanostructures including CNTs preferably have an average length at the time of synthesis of 100 µm or more. Fibrous carbon nanostructures having a longer length at the time of synthesis are more susceptible to damage to CNTs by breaking, severing or the like during dispersing. Therefore, the average length of the nanostructures at the time of synthesis is preferably 5,000 µm or less.

The fibrous carbon nanostructures including CNTs preferably have an aspect ratio (length/diameter) of greater than 10. The aspect ratio of the fibrous carbon nanostructures can be found by measuring diameters and lengths of 100 fibrous carbon nanostructures randomly-selected by transmission electron microscopy and calculating the average of ratios of length to diameter (length/diameter).

The fibrous carbon nanostructures including CNTs preferably have a BET specific surface area of 600 m$^2$/g or more, more preferably 800 m$^2$/g or more, and preferably 2,500 m$^2$/g or less, more preferably 1,200 m$^2$/g or less. A BET specific surface area of 600 m$^2$/g or more allows for sufficient increases in electrical conductivity and flexibility of the silicone rubber composition. A BET specific surface area of 2,500 m$^2$/g or less can limit aggregation of the fibrous carbon nanostructures to increase the dispersibility of the fibrous carbon nanostructures in the silicone rubber composition.

As used herein, "BET specific surface area" refers to a nitrogen adsorption specific surface area measured by the BET method.

In accordance with the super growth method described later, the fibrous carbon nanostructures including CNTs are obtained, on a substrate having thereon a catalyst layer for carbon nanotube growth, in the form of an aggregate wherein fibrous carbon nanostructures are aligned substantially perpendicularly to the substrate (aligned aggregate). The mass density of the fibrous carbon nanostructures in the form of such an aggregate is preferably 0.002 g/cm$^3$ to 0.2 g/cm$^3$. A mass density of 0.2 g/cm$^3$ or less allows the fibrous carbon nanostructures to be homogeneously dispersed within the silicone rubber composition because binding among the fibrous carbon nanostructures is weakened. A mass density of 0.002 g/cm$^3$ or more improves the unity of the fibrous carbon nanostructures thus preventing the fibrous carbon nanostructures from becoming unbound and making the fibrous carbon nanostructures easier to handle.

The fibrous carbon nanostructures including CNTs preferably include micropores. In particular, the fibrous carbon nanostructures preferably include pores that have a pore diameter of smaller than 2 nm. The abundance of these micropores as measured in terms of micropore volume determined by the method described below is preferably 0.40 mL/g or more, more preferably 0.43 mL/g or more, even more preferably 0.45 mL/g or more, with the upper limit being generally on the order of 0.65 mL/g. The presence of such micropores in the fibrous carbon nanostructures including CNTs limits aggregation of the fibrous carbon nanostructures so that a silicone rubber composition can be obtained that contains fibrous carbon nanostructures highly dispersed therein. Micropore volume can be adjusted for example by appropriate alteration of the production method and the production conditions of the fibrous carbon nanostructures including CNTs.

"Micropore volume (Vp)" can be calculated using Equation (I): $Vp=(V/22414)\times(M/\rho)$ by measuring a nitrogen adsorption isotherm of the fibrous carbon nanostructures including CNTs at liquid nitrogen temperature (77 K) with the amount of adsorbed nitrogen at a relative pressure P/P0 of =0.19 defined as V, where P is a measured pressure at adsorption equilibrium, and P0 is a saturated vapor pressure of liquid nitrogen at time of measurement. In Equation (I), M is a molecular weight of 28.010 of the adsorbate (nitrogen), and ρ is a density of 0.808 g/cm$^3$ of the adsorbate (nitrogen) at 77 K. Micropore volume can be measured for example using BELSORP®-mini (BELSORP is a registered trademark in Japan, other countries, or both) produced by Bel Japan Inc.

The fibrous carbon nanostructures including CNTs having the properties described above can be efficiently produced for example by forming a catalyst layer on a substrate surface by wet process in the super growth method (see WO2006/011655) wherein during synthesis of CNTs through chemical vapor deposition (CVD) by supplying a feedstock compound and a carrier gas onto a substrate having thereon a catalyst layer for carbon nanotube production, the catalytic activity of the catalyst layer is dramatically improved by providing a trace amount of an oxidizing agent (catalyst activating material) in the system. Hereinafter, carbon nanotubes obtained by the super growth method may also be referred to as "SGCNTs."

The fibrous carbon nanostructures including CNTs produced by the super growth method may be composed solely of SGCNTs or may be composed of SGCNTs and electrically conductive non-cylindrical carbon nanostructures. Specifically, the fibrous carbon nanostructures including CNTs may include single- or multi-walled flattened cylindrical carbon nanostructures having over the entire length a "tape portion" where inner walls are in close proximity to each other or bonded together (hereinafter such carbon nanostructures are occasionally referred to as "graphene nanotapes (GNTs)").

The phrase "having over the entire length a tape portion" as used herein refers to "having a tape portion over 60% or more, preferably 80% or more, more preferably 100% of the length of the longitudinal direction (entire length), either continuously or intermittently."

GNT is presumed to be a substance having over the entire length a tape portion where inner walls are in close proximity to each other or bonded together since it has been synthesized, and having a network of 6-membered carbon rings in the form of flattened cylindrical shape. GNT's flattened cylindrical structure and the presence of a tape portion where inner walls are in close proximity to each other or bonded together in the GNT can be confirmed for example as follows: GNT and fullerene (C60) are sealed into a quartz tube and subjected to heat treatment under reduced pressure (fullerene insertion treatment) to form a fullerene-inserted GNT, followed by observation under transmission electron microscopy (TEM) of the fullerene-inserted GNT to confirm the presence of part in the GNT where no fullerene is inserted (tape portion).

The shape of the GNT is preferably such that it has a tape portion at the central part in the width direction. More preferably, the shape of a cross-section of the GNT, perpendicular to the extending direction (axial direction), is such that the maximum dimension in a direction perpendicular to the longitudinal direction of the cross section is larger in the vicinity of opposite ends in the longitudinal direction of the cross section than in the vicinity of the central part in the longitudinal direction of the cross section. Most preferably, a cross-section of the GNT perpendicular to the extending direction (axial direction) has a dumbbell shape.

The term "vicinity of the central part in the longitudinal direction of a cross section" used for the shape of a cross section of GNT refers to a region within 30% of longitudinal dimension of the cross section from the line at the longitudinal center of the cross section (i.e., a line that passes through the longitudinal center of the cross section and is perpendicular to the longitudinal line in the cross section). The term "vicinity of opposite ends in the longitudinal direction of a cross section" refers to regions outside the "vicinity of the central part in the longitudinal direction of a cross section" in the longitudinal direction.

Carbon nanostructures including GNTs as non-cylindrical carbon nanostructures can be obtained by, when synthesizing CNTs by the super growth method using a substrate having thereon a catalyst layer (hereinafter occasionally referred to as a "catalyst substrate"), forming the catalyst substrate using a specific method. Specifically, carbon nanostructures including GNTs can be obtained by the super growth method using a catalyst substrate prepared as follows: coating liquid A containing an aluminum compound is applied on a substrate and dried to form an aluminum thin film (catalyst support layer) on the substrate, followed by application of coating liquid B containing an iron compound on the aluminum thin film and drying of the coating liquid B at a temperature of 50° C. or below to form an iron thin film (catalyst layer) on the aluminum thin film.

The silicone rubber composition preferably comprises the fibrous carbon nanostructures including CNTs at an amount of 1% by mass or more, more preferably 3% by mass or more, even more preferably 3.5% by mass or more, particularly preferably 5% by mass or more, and preferably 10% by mass or less, more preferably 7% by mass or less. When the silicone rubber composition comprises the fibrous carbon nanostructures including CNTs at an amount of 1% by mass or more, it is possible to sufficiently increase the electrical conductivity of the silicone rubber composition. When the silicone rubber composition comprises the fibrous carbon nanostructures including CNTs at an amount of 10% by mass or less, it is possible to limit rises in hardness (i.e., reductions in flexibility) of the silicone rubber composition, so that a silicone rubber composition can be obtained that has sufficiently high levels of electrical conductivity and flexibility at the same time.

(Electrically Conductive Materials)

Any of the electrically conductive materials known in the art can be used as an electrically conductive material other than the fibrous carbon nanostructures described above. In particular, it is preferred to use graphite as such an electrically conductive material.

Examples of graphite include artificial graphite, flake graphite, flaked graphite, natural graphite, acid-treated graphite, expandable graphite, and expanded graphite. These types of graphite may be used alone or in combination.

In particular, it is preferred to use expanded graphite as the electrically conductive material because the electrical conductivity of the silicone rubber composition can be further increased.

Expanded graphite which may be suitably used as an electrically conductive material can be obtained for example by thermal expansion of expandable graphite which has been obtained by chemical treatment of graphite such as flake graphite with sulfuric acid or the like, followed by micronization. Examples of expanded graphite include EC1500, EC1000, EC500, EC300, EC100, and EC50 (all trade names) available from Ito Graphite Co., Ltd.

The silicone rubber composition preferably comprises the electrically conductive material at an amount of 5% by mass or more, more preferably 10% by mass or more, even more preferably 20% by mass or more, and preferably 35% by mass or less, more preferably 25% by mass or less. When the silicone rubber composition comprises the electrically conductive material at an amount of 5% by mass or more, it is possible to sufficiently increase the electrical conductivity of the silicone rubber composition. When the silicone rubber composition comprises the electrically conductive material at an amount of 35% by mass or less, it is possible to limit rises in hardness (i.e., reductions in flexibility) of the silicone rubber composition, so that a silicone rubber composition can be obtained that has sufficiently high levels of electrical conductivity and flexibility at the same time.

(Additional Additives)

Any of the additives commonly blended into rubber compositions, such as cross-linking agents and antioxidants, can be used. Hardness modifiers such as silicone oils can also be used as such additional additives. Any amount of additional additives can be blended as long as the effect of the present disclosure is not significantly compromised.

Examples of cross-linking agents include peroxide-based cross-linking agents, polyol-based cross-linking agents, thiocyanate-based cross-linking agents, and platinum compound-based cross-linking agents.

Examples of antioxidants include phenol-based antioxidants, phosphorus-based antioxidants, and sulfur-based antioxidants.

(Method of Preparing Silicone Rubber Composition)

The disclosed silicone rubber composition can be prepared for example by mixing or kneading a silicone rubber, fibrous carbon nanostructures including CNTs, and as optional components, an electrically conductive material other than fibrous carbon nanostructures and additional additives, at a desired ratio.

The method of preparing the silicone rubber composition by mixing the components described above comes in the following two forms, for example:

Method (1) that involves dissolution of the silicone rubber in an organic solvent, dispersing of the fibrous carbon nanostructures including CNTs in the organic solvent and mixing of the optional components in the organic solvent, followed by removal of the organic solvent; and Method (2) that involves dispersing of the silicone rubber in a silicone rubber-insoluble solvent, dispersing of the fibrous carbon nanostructures including CNTs in the solvent and mixing of the optional components in the solvent, followed by removal of the solvent.

In both Methods (1) and (2), mixing of the components can be accomplished as follows, for example: the silicone rubber and solvent are placed in a single container and mixed with optional stirring, after which the fibrous carbon nanostructures including CNTs are added into the silicone rubber-containing solvent and dispersed using a ultrasonic homogenizer, wet jet mill or other mixing devices, and optional components are added and mixed with stirring. Alternatively, in Methods (1) and (2), mixing of the components may be accomplished as follows, for example: the fibrous carbon nanostructures including CNTs are pre-dispersed in a solvent, after which the silicone rubber is added into the dispersion and dissolved or dispersed with optional mixing, and optional components are added and mixed with stirring. Stirring can be carried out using any stirring device known in the art, such as a stirring blade, magnetic stirrer, or planetary mill. Stirring time is preferably from 10 minutes to 24 hours. Solvent removal can be accomplished for example by solidification, casting or drying An example of a method of preparing the silicone rubber composition by kneading the components described above includes Method (3) that involves adding the fibrous carbon nanotubes including CNTs and optional components into the silicone rubber and kneading the mixture without using any solvent.

Kneading can be carried out for example using a mixer, single screw kneader, twin screw kneader, roll, Brabender, extruder or other kneading devices, after the silicone rubber has been molten.

Among the methods described above, from the perspective of improving the dispersibility of the fibrous carbon nanostructures including CNTs and optional components, it is preferred to employ Method (1) to prepare the silicone rubber composition.

The prepared silicone rubber composition can be shaped by any common shaping method, such as press shaping, blow shaping or extrusion shaping, for use in various applications.

(Vulcanized Product)

The silicone rubber composition prepared as described above can also be used in various applications after vulcanized and shaped into a vulcanized product. A vulcanized product obtainable by vulcanization of the disclosed silicone rubber composition having superior electrical conductivity and flexibility exhibits superior electrical conductivity and flexibility.

The vulcanized product obtainable by vulcanization of the disclosed silicone rubber composition preferably has a hardness of 80 or less, more preferably 55 or less. A hardness of 80 or less allows sufficient adhesion and shape conformability to be ensured during use.

The vulcanized product obtainable by vulcanization of the disclosed silicone rubber composition preferably has a volume resistivity of $10^5$ $\Omega$·cm or less, more preferably 2,000 $\Omega$·cm or less, more preferably 500 $\Omega$·cm or less, particularly preferably 300 $\Omega$·cm or less. When the volume resistivity is $10^5$ $\Omega$·cm or less, the vulcanized product may be suitably used as an electrically conductive material.

In the present disclosure, the "hardness" of the vulcanized product can be measured using a type A durometer in accordance with JIS K 6253-3. The "volume resistivity" of the vulcanized product can be measured using a low resistivity meter in accordance with JIS K 7194.

EXAMPLES

The following provides a more specific description of the present disclosure based on Examples, which however shall not be construed as limiting. In the following description, "%" and "parts" used to express quantities are by mass, unless otherwise specified.

In Examples and Comparative Examples, the hardness and volume resistivity of a vulcanized product were measured or evaluated using the methods described below.

<Hardness>

The prepared silicone rubber composition was charged into a mold and vulcanized to mold two cylindrical test specimens (diameter: 2.9 cm, height: 1.25 cm). The primary vulcanization condition was set at 170° C. for 15 minutes and the secondary vulcanization condition was set at 200° C. for 240 minutes.

The hardness of each test specimen was measured using a type A durometer in accordance with JIS K 6253-3, and an average of measured hardness values was calculated and recorded as the hardness of the vulcanized product.

<Volume Resistivity>

The prepared silicone rubber composition was charged into a mold and vulcanized to mold a rubber sheet (dimensions: 7.5 cm×7.5 cm). The primary vulcanization condition was set at 170° C. for 15 minutes and the secondary vulcanization condition was set at 200° C. for 240 minutes.

Next, from the prepared rubber sheet, four 20 mm×20 mm square test specimens were cut out for use as measurement samples.

Volume electrical conductivity of each sample was measured by a method in accordance with JIS K 7194 using a low resistivity meter (Loresta® MCP-T610 (Loresta is a registered trademark in Japan, other countries, or both), Mitsubishi Chemical Analytech Co., Ltd.). Specifically, each sample was fixed on an insulation board, a probe is pressed against the center (10 mm in length, 10 mm in width) of the sample, and volume resistivity was measured at random 50 points for each sample by applying a voltage of up to 90V. An average of measured values was calculated and recorded as the volume resistivity of the vulcanized product.

For the four-point probe of the low resistivity meter, PSP probe was selected.

(Preparation of Fibrous Carbon Nanostructures a Including CNTs)

<Fabrication of Catalyst Substrate>

1.9 g of aluminum tri-sec-butoxide, an aluminum compound, was dissolved in 100 mL of 2-propanol as an organic solvent. Further, 0.9 g of triisopropanolamine as a stabilizer was added and dissolved to prepare coating liquid A for forming a catalyst support layer.

In addition, 174 mg of iron acetate, an iron compound, was dissolved in 100 mL of 2-propanol as an organic solvent. Further, 190 mg of triisopropanolamine as a stabilizer was added and dissolved to prepare coating liquid B for forming a catalyst layer.

Coating liquid A was applied by spin coating onto a surface of a base Fe—Cr alloy SUS 430 substrate (JFE Steel Corporation, 40 mm×100 mm, 0.3 mm thickness, 18% Cr, arithmetic mean roughness Ra≈0.59 μm) in an environment of room temperature of 25° C. and 50% relative humidity. Specifically, 0.1 mL of coating liquid A was dropped onto the substrate and the substrate was rotated at 500 rpm for 10 seconds and then at 2,000 rpm for 20 seconds. Thereafter, coating liquid A was air-dried for 5 minutes, heated in an air environment at 300° C. for 30 minutes, and then cooled to room temperature to form an alumina thin film (catalyst support layer) on the substrate.

Subsequently, in an environment of room temperature of 25° C. and 50% relative humidity, coating liquid B was applied by spin coating onto the alumina thin film provided on the substrate. Specifically, 0.1 mL of coating liquid B was dropped on the substrate having the alumina thin film, and then the substrate was rotated at 500 rpm for 10 seconds and then at 2,000 rpm for 20 seconds. Thereafter, by air drying (drying temperature: 30° C.) for 5 minutes, an iron thin film (catalyst layer) was formed. In this way, a catalyst substrate having, in order, an alumina thin film and an iron thin film on a substrate was obtained.

<Synthesis of Aggregate of Carbon Nanostructures>

The prepared catalyst substrate was placed in a reaction furnace (kept at a furnace temperature of 750° C., and a furnace pressure of $1.02 \times 10^5$ Pa) of a batch type manufacturing apparatus, and a mixed gas of $N_2$: 100 sccm and $H_2$: 800 sccm was introduced in 10 minutes. Subsequently, in the reactor kept at a furnace temperature of 750° C. and a furnace pressure of $1.02 \times 10^5$ Pa, a mixed gas of $N_2$: 850 sccm, ethylene: 100 sccm and $H_2O$-containing $N_2$ (23% relative humidity): 50 sccm was fed for 10 minutes.

Thereafter, $N_2$: 1,000 sccm was fed into the reaction furnace, and the remaining feedstock gas and catalyst activation substance were removed. In this way an aggregate of fibrous carbon nanostructures was obtained on the catalyst substrate. The fibrous carbon nanostructure aggregate thus produced was then separated from the catalyst substrate to afford fibrous carbon nanostructures A.

Evaluation and analysis of the resulting fibrous carbon nanostructures A confirmed that the yield was 1.9 mg/cm$^2$, G/D ratio was 3.4, density was 0.03 g/cm$^3$, BET specific surface area was 800 m$^2$/g, carbon purity was 99.9%, average diameter (Av) was 2.7 nm, and 3σ/Av was 0.42.

It was also confirmed that 100 fibrous carbon nanostructures A included 46 single- and two-walled carbon nanotubes and 54 single-walled GNTs.

Further, the t-plot of the fibrous carbon nanostructures A was bent having a convex upward shape. S2/S1 was 0.24, and the bending point was at t=0.6 nm.

Example 1

190 g of silicone rubber (SH831 U, Dow Corning Toray Co., Ltd.) was added to 9,800 g of cyclohexane and dissolved by stirring for 48 hours. 10 g of fibrous carbon nanostructures A was added to the resulting silicone rubber solution and stirred for 15 minutes using a stirrer (Labolution® (registered trademark in Japan, other countries, or both), PRIMIX Corporation). Further, using a wet jet mill (L-ES007, Yoshida Kikai Co., Ltd.), the solution containing fibrous carbon nanostructures A was processed at 120 MPa. Thereafter, the jet-milled solution was added dropwise to a mixed solution of 10,000 g 2-propanol and 40,000 g methanol to afford a black solid. After drying the black solid under reduced pressure for 48 hours at 50° C., 1.2 g of a cross-linking agent (RC-4(50P), Dow Corning Toray Co., Ltd.) was added to 150 g of the dried black solid using an open roll to afford a silicone rubber composition.

The hardness and volume resistivity of a vulcanized product were measured using the silicone rubber composition obtained. The results are shown in Table 1.

Example 2

A silicone rubber composition was obtained as in Example 1 except that 60 g of expanded graphite (EC 500, Ito Graphite Co., Ltd.) as an electrically conductive material was added to the jet-milled solution, stirred for 30 minutes with a propeller stirrer, and the solution containing the silicone rubber, fibrous carbon nanostructures A and expanded graphite was added dropwise to a mixed solution of 10,000 g 2-propanol and 40,000 g methanol to afford a black solid.

The hardness and volume resistivity of a vulcanized product were measured using the silicone rubber composition obtained. The results are shown in Table 1.

Examples 3 to 4

Silicone rubber compositions were obtained as in Example 1 except that the silicone rubber was changed to those shown in Table 1 (all from Dow Corning Toray Co., Ltd.).

The hardness and volume resistivity of vulcanized products were measured using the obtained silicone rubber compositions. The results are shown in Table 1.

Example 5

A silicone rubber composition was obtained as in Example 1 except that the amount of fibrous carbon nanostructures A added to the silicone rubber solution was changed to 5.9 g.

The hardness and volume resistivity of a vulcanized product were measured using the silicone rubber composition obtained. The results are shown in Table 1.

Example 6

A silicone rubber composition was obtained as in Example 1 except that the amount of fibrous carbon nanostructures A added to the silicone rubber solution was changed to 2.9 g.

The hardness and volume resistivity of a vulcanized product were measured using the silicone rubber composition obtained. The results are shown in Table 1.

Example 7

A silicone rubber composition was obtained as in Example 2 except that the silicone rubber was changed to one shown in Table 1 (Dow Corning Toray Co., Ltd.), the amount of fibrous carbon nanostructures A added to the silicone rubber solution was changed to 3 g, and the amount of expanded graphite (EC 500, Ito Graphite Co., Ltd.) added to the jet-milled solution was changed to 30 g.

The hardness and volume resistivity of a vulcanized product were measured using the silicone rubber composition obtained. The results are shown in Table 1.

Comparative Example 1

A silicone rubber composition was obtained as in Example 4 except that 120 g of Ketjen Black (EC 300 J, Lion Corporation) was used in place of fibrous carbon nanostructures A.

The hardness and the volume resistivity of a vulcanized product were measured using the silicone rubber composition obtained. The results are shown in Table 1.

Comparative Example 2

A silicone rubber composition was obtained as in Example 1 except that 30 g of Ketjen Black (EC 300 J, Lion Corporation) was used in place of fibrous carbon nanostructures A.

The hardness and the volume resistivity of a vulcanized product were measured using the silicone rubber composition obtained. The results are shown in Table 1.

Comparative Example 3

A silicone rubber composition was obtained as in Example 1 except that fibrous carbon nanostructures B (NC7000, Nanocyl SA) were used in place of fibrous carbon nanostructures A.

The hardness and the volume resistivity of a vulcanized product were measured using the silicone rubber composition obtained. The results are shown in Table 1.

Evaluation and analysis of fibrous carbon nanostructures B (NC7000, Nanocyl SA) confirmed that BET specific surface area was 265 $m^2/g$ and average diameter (Av) was 10.1 nm. Fibrous carbon nanostructures B did not show any radial breathing mode (RBM) peaks in a spectrum measured by Raman spectroscopy, and observation by transmission electron microscopy also confirmed that fibrous carbon nanostructures B are composed of multi-walled carbon nanotubes. Further, the t-plot of fibrous carbon nanostructures B showed a convex downward shape

Comparative Example 4

A silicone rubber composition was obtained as in Example 5 except that fibrous carbon nanostructures B (NC7000, Nanocyl SA) were used in place of fibrous carbon nanostructures A.

The hardness and the volume resistivity of a vulcanized product were measured using the silicone rubber composition obtained. The results are shown in Table 1.

TABLE 1

| | Example 1 | Example 2 | Example 3 | Example 4 | Example 5 | Example 6 | Example 7 | Comparative Example 1 | Comparative Example 2 | Comparative Example 3 | Comparative Example 4 |
|---|---|---|---|---|---|---|---|---|---|---|---|
| Silicone rubber | SH831U | SH831U | SH 851U | SH 871U | SH831U | SH831U | SH 871U | SH871U | SH831U | SH831U | SH831U |
| Fibrous carbon nanostructures A [% by mass] | 5 | 3.8 | 5 | 5 | 3 | 1.5 | 1.3 | — | — | — | — |
| Fibrous carbon nanostructures B [% by mass] | — | — | — | — | — | — | — | — | — | 5 | 3 |
| Expanded graphite [% by mass] | — | 23 | — | — | — | — | 13 | — | — | — | — |
| Ketjen Black [% by mass] | — | — | — | — | — | — | — | 38 | 13 | — | — |
| Hardness [—] | 34 | 37 | 53 | 75 | 33 | 33 | 78 | 85 | 54 | 33 | 32 |
| Volume resistivity [$\Omega \cdot cm$] | 0.455 | 0.0980 | 0.510 | 0.480 | 323 | 2490 | 286 | 1750 | 3330000 | 3270 | 14732 |

It can be seen from Table 1 that Examples 1-7 containing fibrous carbon nanostructures that exhibit a convex upward shape in a t-plot obtained from an adsorption isotherm may attain high levels of flexibility and electrical conductivity at the same time.

INDUSTRIAL APPLICABILITY

According to the present disclosure, it is possible to provide a silicone rubber composition and a vulcanized product thereof, which show high levels of flexibility and electrical conductivity at the same time.

The invention claimed is:

1. A silicone rubber composition comprising:
   a silicone rubber; and
   fibrous carbon nanostructures including carbon nanotubes,
   wherein the fibrous carbon nanostructures are produced by forming an aggregate of fibrous carbon nanostructures on a catalyst substrate and then separating the aggregate from the substrate, and
   the fibrous carbon nanostructures have not undergone carbon nanotubes opening formation treatment and exhibit a convex upward shape in a t-plot obtained from an adsorption isotherm, and
   the t-plot has a bending point in a range of $0.45 \leq t$ (nm)$\leq 1.5$, wherein a position of the bending point is an intersection point of a first straight line fitted to a first part of the t-plot corresponding to a process in which a single molecular adsorption layer is formed and an second straight line fitted to a second part of the t-plot corresponding to a process in which a multi-molecular adsorption layer is formed.

2. The silicone rubber composition of claim 1, wherein total specific surface area S1 and internal specific surface area S2 which are obtained from the t-plot satisfy the condition $0.05 \leq S2/S1 \leq 0.30$.

3. The silicone rubber composition of claim 1, wherein the fibrous carbon nanostructures have an average diameter of 2 nm to 10 nm.

4. The silicone rubber composition of claim 1, further comprising graphite.

5. The silicone rubber composition of claim 1, wherein the fibrous carbon nanostructures have a ratio of a standard deviation ($\sigma$) of diameters multiplied by 3 ($3\sigma$) to average diameter (Av) ($3\sigma$/Av) of greater than 0.20 to less than 0.60.

6. The silicone rubber composition of claim 1, wherein the fibrous carbon nanostructures include single- or multi-walled flattened cylindrical carbon nanostructures having over the entire length a tape portion where inner walls are in close proximity to each other or bonded together.

7. A vulcanized product formed by vulcanization of the silicone rubber composition of claim 1.

8. The vulcanized product of claim 7, wherein the vulcanized product has a hardness of 80 or less.

9. The vulcanized product of claim 7, wherein the vulcanized product has a volume resistivity of $10^5$ $\Omega$·cm or less.

* * * * *